(12) United States Patent
Maruyama et al.

(10) Patent No.: US 7,009,046 B2
(45) Date of Patent: Mar. 7, 2006

(54) LOW-SUBSTITUTED HYDROXYPROPYL CELLULOSE AND AGENT SERVING BOTH AS BINDER AND DISINTEGRANT FOR DRY DIRECT COMPRESSION

(75) Inventors: Naosuke Maruyama, Niigata-ken (JP); Hiroshi Umezawa, Niigata-ken (JP)

(73) Assignee: Shin-Etsu Chemical Co. Ltd., Tokyo (JP)

( * ) Notice: Subject to any disclaimer, the term of this patent is extended or adjusted under 35 U.S.C. 154(b) by 205 days.

(21) Appl. No.: 10/315,324

(22) Filed: Dec. 10, 2002

(65) Prior Publication Data

US 2003/0108604 A1 Jun. 12, 2003

(30) Foreign Application Priority Data

Dec. 11, 2001  (JP) ........................................ 2001-376768

(51) Int. Cl.
 *C08B 11/20* (2006.01)

(52) U.S. Cl. .............................. 536/85; 536/84; 536/88; 536/89

(58) Field of Classification Search .................. 536/85, 536/84, 88, 89
See application file for complete search history.

(56) References Cited

U.S. PATENT DOCUMENTS 3,852,421 A    12/1974 Koyanagi et al.
4,091,205 A  *  5/1978 Onda et al. .................... 536/85

FOREIGN PATENT DOCUMENTS

| EP | 0 957 112 A | 11/1999 |
|---|---|---|
| EP | 1 099 709 A | 5/2001 |
| EP | 1 120 427 A1 | 8/2001 |
| EP | 1 192 942 A2 | 4/2002 |
| JP | 55 137102 A | 10/1980 |
| JP | 01 152103 | 6/1989 |
| JP | 05 163162 A | 6/1993 |
| JP | 7-324101 | 12/1995 |
| JP | 08 229103 A | 9/1996 |
| JP | 10 279601 A | 10/1998 |

* cited by examiner

*Primary Examiner*—James O. Wilson
*Assistant Examiner*—Howard V. Owens, Jr.
(74) *Attorney, Agent, or Firm*—Alston & Bird LLP

(57) ABSTRACT

Provided is an agent serving as a binder and a disintegrant for dry direct compression having a high binding property and fluidity. More specifically, provided are low-substituted hydroxypropyl cellulose having coiled fibers; an agent serving both as a binder and a disintegrant for dry direct compression and a solid preparation, each comprising the low-substituted hydroxypropyl cellulose; and a process for producing the low-substituted hydroxypropyl cellulose having coiled fibers.

13 Claims, 2 Drawing Sheets

LOW-SUBSTITUTED HYDROXYPROPYL CELLULOSE AND AGENT SERVING BOTH AS BINDER AND DISINTEGRANT FOR DRY DIRECT COMPRESSION

BACKGROUND OF THE INVENTION

1. Field of the Invention

The present invention relates to low-substituted hydroxypropyl cellulose to be added to impart preparations with disintegrability or a binding property upon their production in the pharmaceutical or food field; and a production process thereof.

2. Description of the Related Art

In the pharmaceutical or food field, solid preparations composed alone of an active ingredient are accompanied with the problems that even the administration of the medicament cannot bring about sufficient effects because they lack in disintegrability, or they cannot retain their shapes when formed into tablets or granules because of a poor binding property. In such a case, addition of low-substituted hydroxypropyl cellulose to the preparations can impart them with disintegrability or a binding property.

In addition to this low-substituted hydroxypropyl cellulose, calcium salt of carboxymethyl cellulose, crosslinked sodium carboxymethylcellulose, crosslinked polyvinylpyrrolidone, and carboxymethyl starch can be given as examples usable for the above-described purpose. Low-substituted hydroxypropyl cellulose has an advantage that since it is nonionic, it is not easily deteriorated by the reaction with an ionic substance.

There are a method of manufacturing tablets by dryly blending low-substituted hydroxypropyl cellulose powder, a medicament and the other ingredients such as excipient and then tableting the resulting mixture; and a method of forming granules by kneading the above-described ingredients with water or an aqueous solution of a water soluble binder and then granulating the resulting mixture. The low-substituted hydroxypropyl cellulose is a medicinal additive included in Japanese Pharmacopoeia and use of it as a medicinal additive has already been described in Japanese Patent Publication (JP-B) No. 46-42792/1971 and Japanese Patent Publication (JP-B) No. 57-53100/1982.

The low-substituted hydroxypropyl cellulose is a mixture of fibrous and granular parts in the powdery form and a binding property required for formation of tablets is said to result from the entanglement of the fibrous part of the mixture. An increase in the content of this fibrous part in order to heighten the binding property, however, makes the powder bulky and lowers its fluidity. In the method of dryly blending low-substituted hydroxypropyl cellulose, a medicament and the other ingredients including excipient and then tableting the resulting mixture, which method is generally called "dry direct compression", this low fluidity causes problems that tableting cannot be performed because the mixture does not come out from the hopper of a tableting machine, or even if tableting can be performed, a weight variation of the tablets becomes excessively large. In Japanese Patent Provisional Publication (JP-A) No. 7-324101/1995, disclosed is low-substituted hydroxypropyl cellulose having a swelling ratio of 100% or greater at an angle of repose of 45° or less. This cellulose has improved fluidity, but involves a problem that a reduction in the amount of a fibrous part leads to lowering in a binding property.

SUMMARY OF THE INVENTION

With the foregoing in view, the present invention has been completed. An object of the present invention is to provide low-substituted hydroxypropyl cellulose which is added as a binder and a disintegrant at the formation of tablets and serves both as a binder and a disintegrant for dry direct compression, wherein the low-substituted hydroxypropyl cellulose is excellent in a binding property and fluidity.

With a view to attaining the above-described object, the present inventors have carried out an extensive investigation. As a result, it has been found that an agent serving both as a binder and a disintegrant for dry direct compression which agent has improved a binding property and fluidity can be obtained by making the fibers of the low-substituted hydroxypropyl cellulose coiled preferably using a granulation method, leading to the completion of the present invention.

In the present invention, there are thus provided low-substituted hydroxypropyl cellulose having coiled fibers, an agent comprising it and serving both as a binder and a disintegrant for dry direct compression and a production method of low-substituted hydroxypropyl cellulose having coiled fibers.

The low-substituted hydroxypropyl cellulose having coiled fibers can be used as a base for dry direct compression, serving both a binder and a disintegrant having high a binding property and fluidity.

DETAILED DESCRIPTION OF THE PREFERRED EMBODIMENTS

Figure 1:
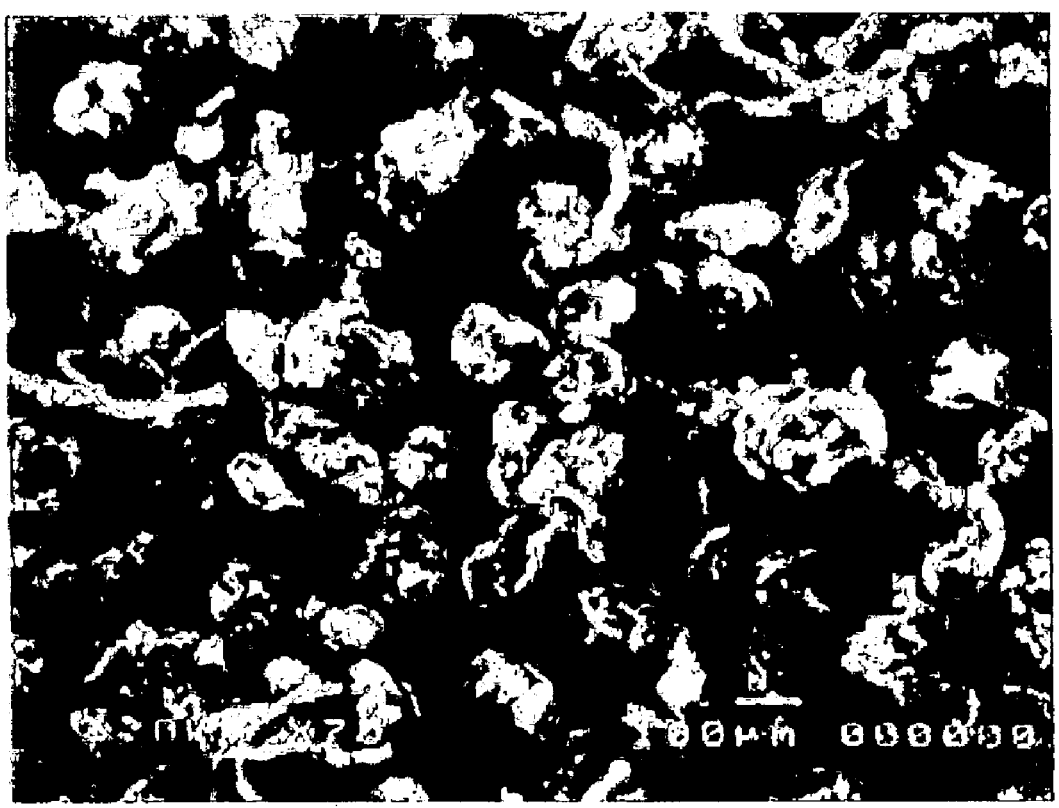
FIG. 1 exhibits an SEM photograph (75×) of low-substituted hydroxypropyl cellulose prepared in Example 1.

The present invention will hereinafter be described more specifically.

The term "agent serving both as binder and a disintegrant for dry direct compression" of the present invention means an agent serving both as a binder and a disintegrant to be used in production of tablets or the like by the dry method. The dry direct compression is a method for preparing tablets or the like comprising steps of mixing a medicament and one or more selected from an excipient, a binder and a disintegrant, each in the powdery form, without using water or a solvent and then subjecting the resulting mixture to compression molding by a tableting machine. This method has a merit in its simple process, because the powdery components can be compression molded only after mixing.

In the low-substituted hydroxypropyl cellulose for use in the present invention, the molar substitution of hydroxypropoxyl groups per anhydrous glucose unit ranges from 0.1 to 0.5. When the molar substitution of hydroxypropoxyl groups is less than 0.1, the binding property does not reach the intended level, while at the molar substitution exceeding 0.5, the disintegrability does not reach the intended level and disintegration time of the resulting tablets is prolonged.

The low-substituted hydroxypropyl cellulose of the present invention needs high fluidity, because in dry direct compression, powders are fed continuously from the hopper of a tableting machine. Its fluidity index is preferably 60 or greater. Although no particular limitation is imposed on the upper limit of the fluidity index insofar as a sufficient binding property can be attained at such a fluidity index, that of approximately 80 is especially preferred.

The above-described "fluidity index" means a index of powder fluidity proposed by Carr. The fluidity index is determined by measuring, in addition to the compressibility found by the below-described equation, angle of repose, angle of spatula and uniformity coefficient, finding their indices from these four values and then adding up these indices. Details are described in "Kaitei Zoho Funtai Bussei Zusetsu (Revised and Enlarged Edition, Physical Properties of Powder With Illustrations)", p151(1985), compiled by The Society of Powder Technology Japan and The Association of Powder Process Industry and Engineering, Japan, published by NGT Corporation.

Compressibility(%)={(tapped bulk density−loose bulk density)/tapped bulk density}×100

The angle of repose is obtained by dropping a powder from a height of 11 cm through a JIS 22 mesh (710 μm) sieve and a following funnel having a diameter of 0.5 cm and measuring a angle between a summit and a table.

The angle of spatula is

In the above-described equation, the term "loose bulk density" means the bulk density in a loosely filled state and it can be measured by uniformly charging a cylindrical vessel having a diameter of 5.03 cm and a height of 5.03 cm (volume: 100 ml) with a sample through a sieve of 22 mesh (710 μm) of Japanese Industrial Standard (JIS) from an upper part thereof (23 cm above the vessel); removing any excess powder over the level of the upper surface; and weighing the sample filled in the vessel. Most typically, "Powder Tester (PT-D)" (trade name; product of Hosokawa Micron Co., Ltd.) can be used for the measurement.

The tapped bulk density can be measured by fitting an exclusive cap, which is an attachment of "Powder Tester" of Hosokawa Micron, on the upper part of the vessel used for measuring loose bulk density; further adding the sample up to the upper edge of the cap; tapping the vessel 180 times from the height of 1.8 cm; with the cap off, removing any excess powder over the level of the upper surface; and weighing the sampled filled in the 100-ml vessel.

The angle of pose, angle of spatula and uniformity coefficient can be obtained in reference to R. L. Carr, Jr., Chemical Engineering, pp. 163–168, Jan. 18, 1965.

The angle of pose can be obtained by dropping powder from 11 cm above a table through a JIS 22-mesh sieve (710 μm) and then through a funnel with 0.5 cm diameter onto the horizontal table with 8 cm diameter; and measuring the angle between a summit of the accumulated powder and the horizontal table.

The angle of spatula can be obtained by holding a spatula with a blade (10 cm×2 cm) right on an ascent/descent table; mounting powder on the table; lowering the table so as to leave a pile of powder on the blade; measuring a first angle between a summit of the piled powder and the horizontal table; tapping the spatula by dropping a 5 g weight from 10 cm above the spatula onto the edge thereof; measuring a second angle between a summit of the piled powder and the horizontal table; and averaging the first and second angles.

The uniformity coefficient is the ratio of $D_{60}/D_{10}$ based on measurement of a particle size distribution. The $D_{10}$ and $D_{60}$ are defined in such a way that, when the particle size distribution of the powder is measured and the detection frequencies of various particle diameters are integrated from the smaller diameter to the larger diameter, the particle diameters corresponding to 10% and 60% of all particles are represented by $D_{10}$ and $D_{60}$, respectively. The particle size distribution can be measured using different sizes of sieves or a laser diffraction analyzer. For example, when the sieves are used, the sieves having different opening diameters are piled vertically keeping them in order of the sieves having smaller openings toward the bottom of the pile. The 50 g of sample is placed on the top sieve with the largest openings and shaken together with sieves for twenty minutes. Subsequently, the weight of the powder left on each sieve can be measured to yield the particle size distribution.

The low-substituted hydroxypropyl cellulose is usually a mixture of a fibrous portion and a granular portion. Its binding property result from the former one, while the disintegrability results from the latter one. The fluidity of the low-substituted hydroxypropyl cellulose can be enhanced by taking an advantage of the cellulose being soluble in an aqueous alkali solution. More specifically, improvement in fluidity can be attained by dissolving in water an alkali-containing low-substituted hydroxypropyl cellulose reaction product which inherits the fibrous form of the raw material pulp, neutralizing the resulting solution with an acid to yield precipitation, thereby converting the fibrous form to the granular form. However, the low-substituted hydroxypropyl cellulose in the granular form thus obtained by dissolution after neutralization has a dense structure so that the binding property for compression molding is lowered.

On the other hand, according to the low-substituted hydroxypropyl cellulose of the present invention, linear fibers existing among fibrous and granular forms have been coiled. These coiled linear fibers are apparently spherical and therefore, excellent in fluidity. When such low-substituted hydroxypropyl cellulose is compression molded, the fibers contribute to the higher binding property.

The binding property, usable as an index, can be evaluated based on breaking strength in the longer axis direction of a tablet of 10 mmØ obtained by compression molding 200 g of low-substituted hydroxypropyl cellulose at 9.8 Mpa for 30 minutes by using an IR (infrared) tableting machine. This strength is usually called tablet hardness. A preferable binder for dry direct compression can yield tablet hardness of 130N or greater, more preferably 150N or greater. Although no particular limitation is imposed on the upper limit of this tablet hardness insofar as a disintegration property can be attained, tablet hardness not greater than 300N is especially preferred.

The low-substituted hydroxypropyl cellulose of the present invention can be prepared by granulating the washed product of low-substituted hydroxypropyl cellulose. No particular limitation is imposed on the washed product of low-substituted hydroxypropyl cellulose and a known method can be adopted for the preparation of low-substituted hydroxypropyl cellulose.

In an embodiment, an alkali cellulose prepared by immersing pulp in an aqueous solution of caustic soda and being subsequently compressed, is reacted with propylene oxide. In another embodiment, propylene oxide is added to an alkali cellulose prepared by adding an aqueous solution of caustic soda to a solution of powdery pulp in an organic solvent such as isopropyl alcohol, tert-butyl alcohol, hexane or the like, whereby low-substituted hydroxypropyl cellulose can be obtained as a reaction product.

The low-substituted hydroxypropyl cellulose is soluble in an aqueous alkali solution and caustic soda used as a catalyst remains in its reaction product. After addition of water to the reaction product to dissolve the latter in the former, the remaining alkali is neutralized with an acid (for example, acetic acid, hydrochloric acid or sulfuric acid) to yield neutralized and precipitated particles of low-substituted hydroxypropyl cellulose.

The salt formed in the above-described step and the other impurities are washed off with water or hot water, followed by removal of water, whereby washed low-substituted hydroxypropyl cellulose is obtained.

The conventional low-substituted hydroxypropyl cellulose is obtained by drying and pulverizing the washed low-substituted hydroxypropyl cellulose. Accordingly to the present invention, however, granulation of the washed low-substituted hydroxypropyl cellulose prior to these steps is carried out.

Examples of a granulator to be used for the granulation of the washed low-substituted hydroxypropyl cellulose include a vertical agitation granulator, a horizontal agitation granulator, a batch type kneader, a horizontal short-shaft continuous kneader, and a horizontal double-shaft continuous kneader. Of these, a horizontal double-shaft continuous kneader is preferred. In the continuous kneader, apparent density and fluidity of the product can be controlled by the dwelling time of the washed product in the kneader.

When such a continuous kneader is used, the dwelling time can be regulated by varying the arrangement of built-in paddles, the rotational speed, the opening of the outlet port and the like. The dwelling time can be measured by adding a pigment at the inlet port, sampling the granulated reaction product coming out of the outlet port with time, and determining the average dwelling time at which the highest pigment concentration is exhibited. Although the dwelling time may vary according to the desired apparent density of the product, it generally falls within a range of about 30 to 300 seconds.

Such a continuous kneader can reduce the granulation time and thereby improve the treating rate as compared with batch type mixers. Moreover, since the treatment can be carried out using a small-sized equipment, the equipment cost and an area of the installment site can be reduced.

The continuous kneader usable in the present invention can include single-shaft type, double-shaft type and the like. The double-shaft type is preferred in the present invention because of excellent kneading properties. In such a kneader, the dwelling time or the degree of kneading can be controlled by the combination of built-in paddles. The continuous kneader having an L/D ratio, which is a ratio of the trough length to the paddle diameter, falling within a range of about 5 to 13 can be used.

The influence of the granulation temperature on the physical properties of the product is not so large that it can be freely selected. The granulate can be dried in a conventional manner and the dried granulates may be pulverized or classified as needed. The drying method, which is not particularly limited, includes drying with a hot air oven at about 60 to 80° C. and drying at an inlet air temperature of about 60 to 80° C. in a fluidized bed dryer.

The low-substituted hydroxypropyl cellulose thus obtained serves both as a binder and a disintegrant for dry direct compression. It has improved a binding property and fluidity. A solid preparation such as tablet can be produced by mixing the low-substituted hydroxypropyl cellulose of the present invention and a medicament, each in the powdery form, and compression molding the resulting mixture by a tableting machine. The content of the low-substituted hydroxypropyl cellulose may vary depending on the kind of the medicament or dosage form, but may be preferably 5 to 30% by weight in the solid preparation. The average particle size of the low-substituted hydroxypropyl cellulose powder of the present invention to be mixed my be determined in consideration of the other powdery components such as medicament and excipient, but may be preferably 50 to 300 µm.

The present invention will hereinafter be described in details by Examples and Comparative Examples. The present invention is not restricted to the contents of Examples.

EXAMPLE 1

An alkali cellulose having a composition of 22.2 wt % of NaOH, 44.8 wt % of cellulose and 33.0 wt % of $H_2O$ was obtained by immersing pulp in a 43 wt % solution of caustic soda, followed by compression. In a reactor having a capacity of 5 L was charged 350 g, in terms of cellulose, of the alkali cellulose and the reactor was purged with nitrogen. Then, 79 g (0.226 part by weight relative to 1 part by weight of cellulose) of propylene oxide was added and reacted at a jacket temperature of 45° C. for 2 hours and 65° C. for 30 minutes. The 857 g of the crude reaction product of hydroxypropyl cellulose (a molar substitution of hydroxypropoxyl groups per anhydrous glucose unit: 0.25) was obtained.

In a 5 L batch type kneader, 1925 g of 45° C. water and 52 g of glacial acetic acid were charged. The whole amount of the crude reaction product was added therein and dissolved. To the resulting solution was added 633 g of 33 wt % acetic acid at a rate of 20 g/minute to neutralize the solution and cause precipitation. The neutralized precipitate was washed by the addition of hot water to form slurry and the subsequent dehydration in a centrifugal dehydrator. The washed product was granulated at a rate of 300 g/minute in a double-shaft continuous kneader ("KRC kneader Model S2", product of KURIMOTO, LTD., paddle diameter: 50 mmØ, barrel length: 660 mm, L/D: 13.2, internal volume: 1.2 L) at rotational speed of 100 rpm, dwelling time of 105 seconds and jacket temperature of 60° C.

The granulate thus obtained was dried for one day and one night in a hot air oven at 80° C., pulverized, and sifted through a 150-mesh sieve (opening: 100 µm). The powder left on the sieve was collected as a target product. The fluidity index, binding property and disintegrability thereof are shown in Table 1.

EXAMPLE 2

An alkali cellulose having a composition of 22.2 wt % of NaOH, 44.8 wt % of cellulose and 33.0 wt % of $H_2O$ was obtained by immersing pulp in a 43 wt % solution of caustic soda, followed by compression. In a reactor having a capacity of 5 L was charged 350 g, in terms of cellulose, of the alkali cellulose and the reactor was purged with nitrogen. Then, 79 g (0.226 part by weight relative to 1 part by weight of cellulose) of propylene oxide was added and reacted at a jacket temperature of 45° C. for 2 hours and 65° C. for 30 minutes. The 857 g of the crude reaction product of hydroxypropyl cellulose (a molar substitution of hydroxypropoxyl groups per anhydrous glucose unit: 0.25) was obtained.

In a 5 L batch type kneader, 1925 g of 45° C. water and 52 g of glacial acetic acid were charged. The whole amount of the crude reaction product was added therein and dissolved. To the resulting solution was added 633 g of 33 wt % acetic acid at a rate of 20 g/minute to neutralize the solution and cause precipitation. The neutralized precipitate was washed by the addition of hot water to form slurry and the subsequent dehydration in a centrifugal dehydrator. The washed product was granulated at a rate of 300 g/minute in a double-shaft continuous kneader ("KRC kneader Model S2", product of KURIMOTO, LTD., paddle diameter: 50 mmØ, barrel length: 660 nm, L/D: 13.2, internal volume: 1.2 L) at rotational speed of 100 rpm, dwelling time of 105 seconds and jacket temperature of 60° C.

The granulate thus obtained was dried for one day and one night in a hot air oven at 80° C., pulverized, and sifted through a 150-mesh sieve (opening: 100 µm). The powder which had passed through the sieve was collected as a target product. The fluidity index, binding property and disintegrability thereof are shown in Table 1.

EXAMPLE 3

In a 5 L batch type kneader, 2450 g of 45° C. water and 104 g of glacial acetic acid were charged. The whole amount of the crude reaction product prepared in a similar manner to Example 1 was added therein and dissolved. To the resulting solution was added 468 g of 33% acetic acid at a rate of 20 g/minute to neutralize the solution and cause precipitation. The neutralized precipitate was washed by the addition of hot water and the subsequent dehydration in a centrifugal dehydrator. The washed product was granulated at a rate of 300 g/minute in a double-shaft continuous kneader ("KRC kneader Model S2", product of KURIMOTO, LTD, paddle diameter: 50 mmØ, barrel length: 660 nm, L/D: 13.2, internal volume: 1.2 L) at rotational speed of 100 rpm, dwelling time of 105 seconds and jacket temperature of 60° C.

The granulate thus obtained was dried for one day and one night in a hot air oven at 80° C., pulverized, and sifted through a 150-mesh sieve (opening: 100 µm). The powder which had passed through the sieve was collected as a target product. The fluidity index, binding property and disintegrability thereof are shown in Table 1.

Comparative Example 1

An alkali cellulose having a composition of 22.2 wt % of NaOH, 44.8 wt % of cellulose and 33.0% of $H_2O$ was obtained by immersing pulp in a 43 wt % caustic soda solution, followed by compression. In a reactor having a capacity of 5 L was charged 350 g, in terms of cellulose, of the alkali cellulose and the reactor was purged with nitrogen. Then, 79 g (0.226 part by weight relative to 1 part by weight of cellulose) of propylene oxide was added and reacted at a jacket temperature of 45° C. for 2 hours and 65° C. for 30 minutes. The 857 g of the crude reaction product of hydroxypropyl cellulose (a molar substitution of hydroxypropoxyl groups per anhydrous glucose unit: 0.25) was obtained. In a 5 L batch type kneader, 1925 g of 45° C. water and 104 g of glacial acetic acid were charged. The whole amount of the crude-reaction product was added therein and dissolved. To the resulting solution was added 473 g of 33 wt % acetic acid at a rate of 20 g/minute to neutralize the solution and cause precipitation. The neutralized precipitate was washed by the addition of hot water to form slurry and the subsequent dehydration in a centrifugal dehydrator.

The washed product was dried for one day and one night in a hot air oven at 80° C., pulverized, and sifted through a 150-mesh sieve (opening: 100 µm). The powder which had passed through the sieve was collected as a target product. The fluidity index, binding property and disintegrability thereof are shown in Table 1.

Comparative Example 2

In a 5 L batch type kneader, 2450 g of 45° C. water was charged. The whole amount of the crude reaction product obtained in a similar manner to that employed in Example 1 was added therein and dissolved. To the resulting solution was added 780 g of 33% acetic acid at a rate of 20 g/minute to neutralize the solution and cause precipitation. The neutralized precipitate was washed by the addition of hot water to form slurry and the subsequent dehydration in a centrifugal dehydrator.

The washed product was dried for one day and one night in a hot air oven at 80° C., pulverized, and sifted through a 150-mesh sieve (opening: 100 µm). The powder which had passed through the sieve was collected as a target product. The fluidity index, binding property and disintegrability thereof are shown in Table 1.

The evaluation test methods will be described below.

<Fluidity Index>

Fluidity index was determined by measuring compressibility, angle of pose, angle of spatula and uniformity coefficient by using Powder Tester (product of Hosokawa Micron Co., ltd.) and adding their indices.

<Binding Property>

Tablets of 10 mm in diameter were prepared by weighing 200 mg of each target product and applying pressure to it at 9.8 Mpa for 30 seconds by an IR tableting machine. The hardness of each of the tablets was then measured as binding property.

<Disintegrability>

In accordance with the disintegration test of Japanese Pharmacopoeia 13, disintegration time was measured using 37° C. water as a test liquid. The test results are shown in Table 1.

TABLE 1

|  | Fluidity index | Binding property (N) | Disintegrability (minute) |
|---|---|---|---|
| Ex. 1 | 75 | 151 | 5.1 |
| Ex. 2 | 66 | 178 | 9.2 |
| Ex. 3 | 61 | 198 | 11.5 |
| Comp. Ex. 1 | 45 | 210 | 12.3 |
| Comp. Ex. 2 | 68 | 89 | 4.7 |

From the above-described results, it has been understood that the low-substituted hydroxypropyl cellulose of the present invention is powder having high binding property and excellent fluidity. It can be used as a base for dry direct compression having excellent disintegrability in addition to the above-described property.

Figure 2:
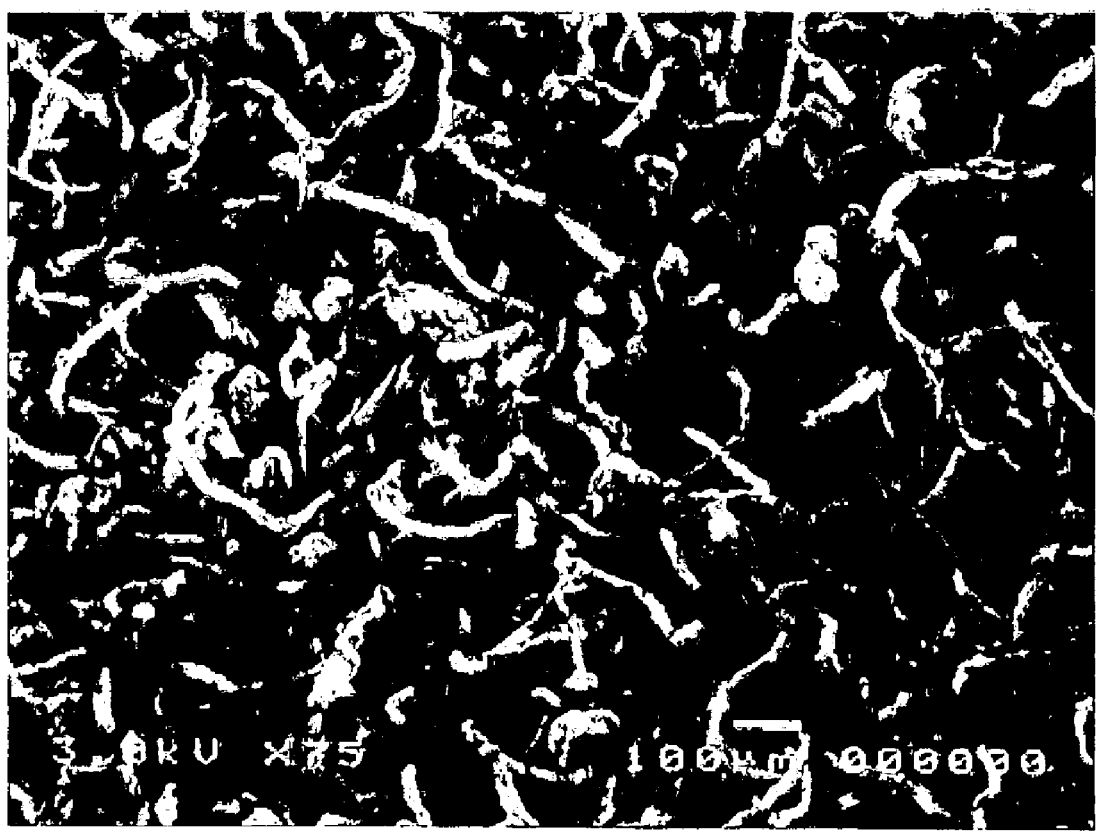
FIG. 2 ehibits an SEM photograph (75×) of low-substituted hydroxypropyl cellulose prepared in Comparative Example 1.

FIGS. 1 and 2 exhibits SEM photographs of the low-substituted hydroxypropyl celluloses obtained in Example 1 and Comparative Example 1. According to the SEM photograph of FIG. 1, fibers of the low-substituted hydroxypropyl cellulose are granulated in the coiled form as the characteristic of the present invention. This low-substituted hydroxypropyl cellulose had high fluidity and a high binding property. The SEM photograph of FIG. 2 shows that the low-substituted hydroxypropyl cellulose is mostly in the fibrous form. It had a high binding property but low fluidity.

What is claimed is:

1. Low-substituted hydroxypropyl cellulose having coiled fibers and having a molar substitution of the hydroxypropoxyl groups ranging from 0.1 to 0.5.

2. Low-substituted hydroxypropyl cellulose according to claim 1 having a fluidity index of 60 or greater.

3. Low-substituted hydroxypropyl cellulose according to claim 1 having 130N or greater tablet hardness wherein the tablet hardness is a breaking strength of a tablet obtained by compression molding of the low-substituted hydroxypropyl cellulose.

4. Low-substituted hydroxypropyl cellulose according to claim 2 having 130N or greater tablet hardness wherein the tablet hardness is a breaking strength of a tablet obtained by compression molding of the low-substituted hydroxypropyl cellulose.

5. An agent serving both as a binder and a disintegrant for dry direct compression, comprising the low-substituted hydroxypropyl cellulose according to claim 1.

6. An agent serving both as a binder and a disintegrant for dry direct compression, comprising the low-substituted hydroxypropyl cellulose according to claim 2.

7. An agent serving both as a binder and a disintegrant for dry direct compression, comprising the low-substituted hydroxypropyl cellulose according to claim 3.

8. An agent serving both as a binder and a disintegrant for dry direct compression, comprising the low-substituted hydroxypropyl cellulose according to claim 4.

9. A solid preparation comprising the agent serving both as a binder and a disintegrant for dry direct compression according to claim 5 and a medicament.

10. A solid preparation comprising the agent serving both as a binder and a disintegrant for dry direct compression according to claim 6 and a medicament.

11. A solid preparation comprising the agent serving both as a binder and a disintegrant for dry direct compression according to claim 7 and a medicament.

12. A solid preparation comprising the agent serving both as a binder and a disintegrant for dry direct compression according to claim 8 and a medicament.

13. A process for producing low-substituted hydroxypropyl cellulose having coiled fibers, comprising granulating, in a kneader, a washed product of low-substituted hydroxypropyl cellulose having a molar substitution of hydroxypropoxyl groups ranging from 0.1 to 0.5.

* * * * *